US009610381B2

United States Patent
Lee et al.

(10) Patent No.: US 9,610,381 B2
(45) Date of Patent: Apr. 4, 2017

(54) PROCESS FOR EXTRACTING NATURAL HYDROXYAPTITE GRANULES FROM BOVINE BONE

(71) Applicant: SIGMAGRAFT, INC., Brea, CA (US)

(72) Inventors: Seung Hyun Lee, Canyon Country, CA (US); Yuni Pai, Brea, CA (US); Katherine Park, Brea, CA (US); Dae Kyu Chang, Brea, CA (US)

(73) Assignee: SIGMAGRAFT, INC., Brea, CA (US)

( * ) Notice: Subject to any disclaimer, the term of this patent is extended or adjusted under 35 U.S.C. 154(b) by 74 days.

(21) Appl. No.: 14/048,356

(22) Filed: Oct. 8, 2013

(65) Prior Publication Data
US 2015/0098875 A1 Apr. 9, 2015

(51) Int. Cl.
*A61L 27/12* (2006.01)

(52) U.S. Cl.
CPC ........... *A61L 27/12* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2,968,593 A | 1/1961 | Espkin | |
| 5,167,961 A | 12/1992 | Geistlich | |
| 8,298,566 B2 | 10/2012 | Markoulides | |
| 2013/0345826 A1* | 12/2013 | Li et al. | 623/23.58 |

FOREIGN PATENT DOCUMENTS

| | | | |
|---|---|---|---|
| CN | 102106765 A | * | 6/2011 |
| WO | WO2004008943 A2 | * | 1/2004 |
| WO | WO 2004054633 A2 | * | 7/2004 |
| WO | WO 2012052035 A1 | * | 4/2012 |

OTHER PUBLICATIONS

Carter, DR, et al., Bone Compressive Strength: The Influence of Density and Strain Rate, Science 194, 1174-1176 (Dec. 1976).*

(Continued)

*Primary Examiner* — Melissa Swain
(74) *Attorney, Agent, or Firm* — Plager Schack LLP

(57) ABSTRACT

A process is for extracting natural hydroxyapatite from bone in order to make granules for a bone graft. The process involves soaking and boiling raw bone cubes in deionized water. Soaking and boiling removes lipids, blood components, and proteins and creates bone cubes. Next, washing the bone cubes in deionized water and drying the bone cubes. Then, segregating cancellous bone cubes with densified porous structure from those without densified porous structure. After that, soaking the cancellous bone cubes with densified porous structure in a solution of sodium hydroxide and a solution of hydrogen peroxide. Next, washing the cancellous bone cubes with densified porous structure in deionized water and drying the bone cubes. Then, sintering the cancellous bone cubes with densified porous structure. After that, fracturing the cancellous bone cubes with densified porous structure into the granules for the bone graft.

14 Claims, 5 Drawing Sheets

(56) References Cited

OTHER PUBLICATIONS

Ramay, H., & Zhang, M. (2004). Biphasic calcium phosphate nanocomposite porous scaffolds for load-bearing bone tissue engineering. Biomaterials (25), 5171-5180.
Borchers, R., Gibson, L., Burchardt, H., & Hayes, W. (1995). Effects of selected thermal variables on the mechanical properties of trabecular bone. Biomaterials (16), 545-551.
Souzanchi, M., Palacio-Mancheno, P., Borisov, Y., Cardoso, L., & Cowin, S. (2012). Microarchitecture and bone quality in the human calcaneus: Local variations of fabric anisotropy. J Bone Miner Res Journal of Bone and Mineral Research 27(12), 2562-2572.
Mcelhaney, J., & Roberts, V. (1971). Mechanical properties of cancellous bone. 9th Aerospace Sciences Meeting.

* cited by examiner

PROCESS FOR EXTRACTING NATURAL HYDROXYAPTITE GRANULES FROM BOVINE BONE

BACKGROUND

The embodiments herein relate generally to the preparation of anorganic substances from bovine bone. In particular, this invention relates to the preparation of natural hydroxyapatite granules with the high specific surface area, the low crude protein content, the multiple pore size, and the high total volumetric porosity using chemical treatment and annealing process with extremely low heating rate at low temperature.

The use of bone grafts in cranio-maxillofacial and dental surgery is growing increasingly. The autografts and the allografts are very effective as bone grafting substitute due to essential physicochemical and biological properties such as their immune response, good osteoinductivity, and osteoconductivity. However, due to the disadvantage of limited supply and availability, alternative biomaterials such as xenografts, which is animal derived source of bone graft or synthetic bone grafts have been proposed and intensively studied.

Specially, among these, the origin of bovine bone grafts has practically unlimited availability and has good physicochemical and structure similar to human bone. Natural hydroxyapatite extracted from bovine bone is almost biocompatible to the human bone due to the properties of osteoconductivity. However, altering the natural structure of hydroxyapatite such as microstructure and pore structure by use of higher temperature can have a negative impact on the physicochemical characterization. This may not be the optimum model to maximize bioresorption and bioactivity. It may also minimize the bone regeneration and healing. Embodiments of the disclosed invention solve these problems. The prior art includes: U.S. Pat. No. 8,298,566 issued to Markoulides; U.S. Pat. No. 5,167,961 issued to Geistlich; and U.S. Pat. No. 2,968,593 issued to Espkin.

Markoulides teaches a process of extracting natural hydroxyapatite from bovine bone comprising: soaking bovine bone in hydrogen peroxide for greater than 20 hours to produce granules with a typical specific surface are of 100 $m^2/g$. Geistlich teaches a process of extracting natural hydroxyapatite from bovine bone comprising: soaking bovine bone in ammonia for 2 to 200 hours to produce granules with a specific surface of, preferably, 120 $m^2/g$ while heat increases from 100 to 350 degrees centigrade. Espkin uses a lower temperature range. However, none of these processes teach washing the bone fragments in deionized water which provides a substantial improvement in the invention described below.

SUMMARY

A process is for extracting natural hydroxyapatite from bone in order to make granules for a bone graft. The process involves soaking and boiling raw bone cubes in deionized water. Soaking and boiling removes lipids, blood components, and proteins and creates bone cubes. Next, washing the bone cubes in deionized water and drying the bone cubes. Then, segregating cancellous bone cubes with densified porous structure from those that have coarsed porous structure. After that, soaking the cancellous bone cubes with densified porous structure in a solution of sodium hydroxide and a solution of hydrogen peroxide. Next, washing the cancellous bone cubes with densified porous structure in deionized water and drying the bone cubes. Then, sintering the cancellous bone cubes with densified porous structure. After that, fracturing the cancellous bone cubes with densified porous structure into the granules for the bone graft.

In some embodiments, drying the bone cubes is done in an oven at a temperature between 60 and 100 degrees centigrade. Soaking the cancellous bone cubes can with densified porous structure in the solution of sodium hydroxide can be done for 1 to 12 hours with between 3 ml and 50 ml of sodium hydroxide used per gram of the cancellous bone cubes with densified porous structure. Soaking the cancellous bone cubes with densified porous structure in the solution of hydrogen peroxide can be done for 6 to 60 hours with between 3 ml and 50 ml of hydrogen peroxide used per gram of the cancellous bone cubes with densified porous structure. Sintering the cancellous bone cubes with densified porous structure can be done at 200-600 degrees centigrade for 1-50 hours with a heating rate of 0.01° C./min to 10° C./min.

In some embodiments, natural hydroxyapatite granules fractured from bone has less than or equal to 400 ppm of crude protein. The natural hydroxyapatite granules fractured from bone can be characterized by an x-ray diffraction pattern comprising peaks expressed in degrees two-theta at about 25 degree, about 30 degree, about 39.5.degree, about 46 degree and about 49 degree. The natural hydroxyapatite granules fractured from bone can have a specific surface area greater than 110 $g/m^2$.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
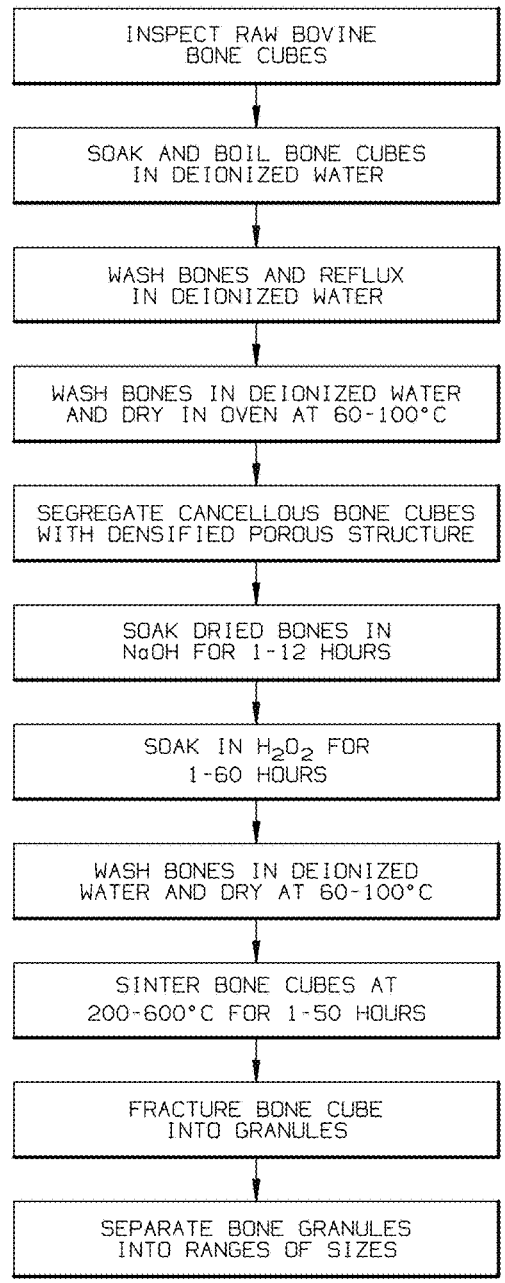
FIG. 1 is a flowchart of an embodiment of the invention.

By way of example, and referring to FIG. 1, one embodiment of the present process includes the following steps, not necessarily in order. Initially, raw bovine bone cubes are inspected for flaws that would render the raw bovine bone cubes otherwise unfit for this process. After inspection, the raw bovine bone cubes are soaked and boiled in deionized water. This removes lipids, blood components, and proteins creating bovine bone cubes. The bovine bone cubes are then washed and refluxed in deionized water rinsing residue, if any from the bones.

Next, the bovine bone cubes are washed in a deionized water and dried in an oven at 60-100 degrees centigrade. Following washing, segregating cancellous bone cubes with densified porous structure from coarsed porous structure.

After this, the cancellous bone cubes with densified porous structure are soaked in a solution of sodium hydroxide for 1-12 hours. Then the cancellous bone cubes with densified porous structure are soaked in a solution of hydrogen peroxide.

Next, and in a substantial deviation from Markoulides, Geistlich, and Espkin, the cancellous bone cubes with densified porous structure are rinsed in deionized water and dried in an oven at a temperature of 60-100 degrees centigrade. Markoulides, Geistlich, and Espkin use a chemical solution to reflux. These chemical solutions distort the polygonal and irregular shape of granules and result in smaller specific surface area.

Following reflux, the cancellous bone cubes with densified porous structure are sintered at 200-600 degrees centigrade for 1-50 hours with a heating rate of 0.01° C./min to 10° C./min. After this the cancellous bone cubes with densified porous structure are fractured into granules into ranges of sizes. The following experimental results were obtained:

EXAMPLE

Sodium hydroxide solution soaking occurred for 1 to 12 hours with between 3 ml and 50 ml of sodium hydroxide used per gram of cancellous bone cubes with densified porous structure. Hydrogen peroxide soaking occurred for 6 to 60 hours with between 3 ml and 50 ml of hydrogen peroxide used per gram of cancellous bone cubes with densified porous structure.

A sintering rate of less than 0.1° C./min was used with a temperature less than 350° C. and a heating time greater than 20 hours. This resulted in specific surface area greater than 110 m$^2$/g, crude protein content less than 400 ppm, and total volumetric porosity greater than 70%.

By way of comparison, Geistlich Bio-Oss® and OCS-B® bone graft were compared to the present invention as these bone grafting materials are widely available in the marketplace, and research has been done on them. See e.g. Hieu, P. D. et al, A radiographical study on the changes in height of grafting materials after sinus lift: a comparison between two types of xenogenic materials, J Periodontal Implant Sci. 2010 February; 40(1): 25-32 (available at: http://synapse.koreamed.org/DOIx.php?id=10.5051/jpis.2010.40.1.25). The following results occurred:

| Grafting material | Present Invention | Geistlich Bio-Oss ® | OCS-B ® |
|---|---|---|---|
| Crude protein (ppm) | 400 ppm | 1180 to 1200 ppm | Pure protein 620 ppm Collagen 500 ppm Other 60 ppm | 530 ppm |

Figure 2A:
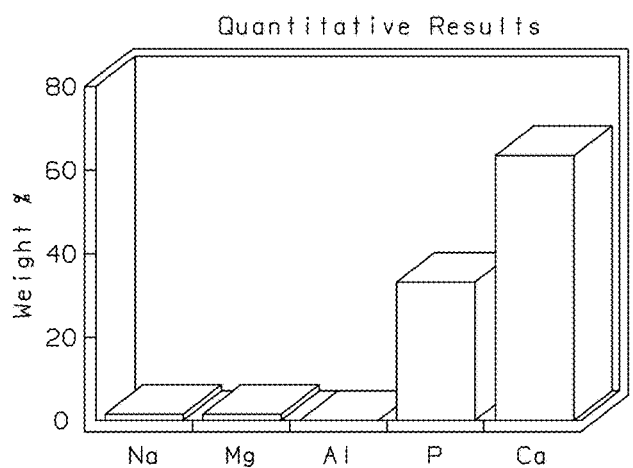
FIG. 2A-2B are graphs of the SEM-EDS of natural hydroxyapatite granules at 350° C. for 20 hours, 0.1° C./min.
Figure 2B:
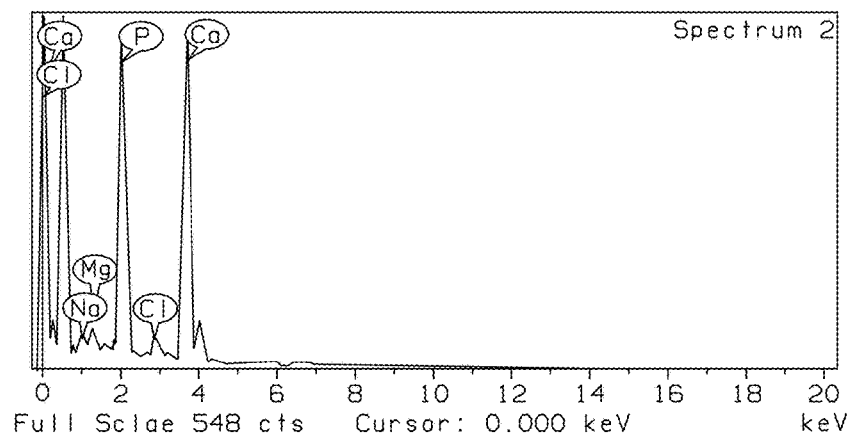

This is also demonstrated in FIG. 2A and FIG. 2B which provide graphs of a Scanning Electron Microscopy with X-ray microanalysis (SEM-EDS) of calcium hydroxyapatite granules at 350° C. for 20 hrs, 0.1° C./min. Calcium hydroxyapatite, $(Ca_{10}(PO_4)_6(OH)_2)$ is one of the biological apatites that comprise inorganic constituents of bone, tooth enamel and dentin, are typically very variable in its composition and morphology. It contains different impurities including $Mg^{2+}$, $K^+$, $Na^+$, $(CO_3)^{2-}$, $(HPO_4.)^{2-}$, $Cl^-$ and $F^-$. In general, these impure biological apatites are designated as calcium deficient or non-stoichiometric apatites. The present process causes prosperous and calcium to compose nearly the entire natural hydroxyapatite granules with only trace amounts of aluminum, magnesium and sodium demonstrating the purity of the bone fragment produced.

The table below compares the Specific Surface Area (m$^2$/g) & Total Porosity (%) of the obtained bone grafts.

| Grafting material | Specific Surface Area (m$^2$/g) | Total Porosity (%) |
|---|---|---|
| Present Invention | 114.4 | 69 |
| Geistlich Bio-Oss ® | 79.7 | 60 |
| OCS-B ® | 63.6 | — |

Figure 3:
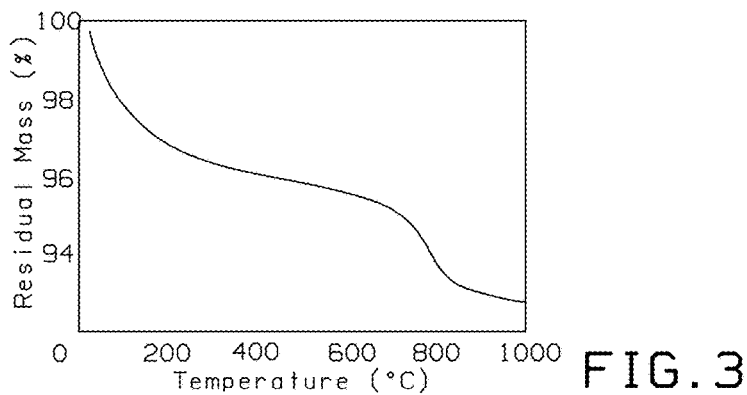
FIG. 3 is a graph of the TGA curve of natural hydroxyapatite granules at 350° C. for 20 hours, 0.1° C./min.

Turning to FIG. 3, a thermogravimetric analysis curve of the natural hydroxyapatite granules, greater specific surface area in the present invention is obtained by using extremely low heating rate and low temperature. This is in contrast to Markoulides, which advocates a higher sintering temperature because lower temperatures would require "Long boiling times [that] would be counterproductive since this would require long washing cycles (typically between 5 and 25 days) for desorption to take place and long sintering times." Unsurprisingly, Markoulides uses higher temperatures that result in lower specific surface area and results almost identical to the Geistlich Bio-Oss® product on the market. Embodiments of the present invention teach away from this process and obtain a better natural and pure granules.

Figure 4:
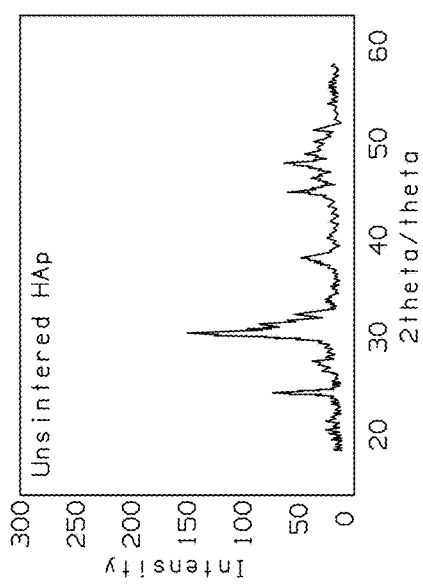
FIG. 4 is a graph of the XRD pattern of natural hydroxyapatite granules at 350° C. for 20 hours, 0.1° C./min.

FIG. 4 shows the cancellous bone cubes with densified porous structure characterized by an x-ray diffraction pattern comprising peaks expressed in degrees two-theta at about 25 degree, about 30 degree, about 39.5.degree, about 46 degree and about 49 degree. This represents a different composition of matter than U.S. Patent application publication 2012/0107373 filed by Shimp which observed an x-ray diffraction pattern comprising peaks expressed in degrees two-theta at about 29.5 degree, about 36.0 degree, about 39.5.degree, about 43.0.degree, and about 57.5.degree when using a different formation method.

Figure 5:
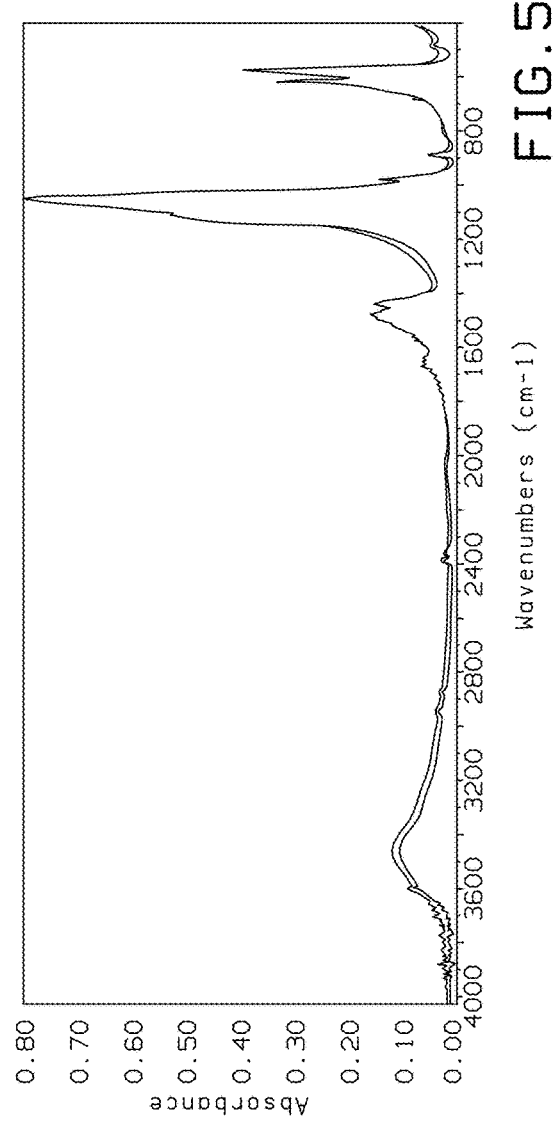
FIG. 5 is a graph of the FTIR trace of natural hydroxyapatite granules at 350° C. for 20 hours, 0.1° C./min.
Figure 6A:
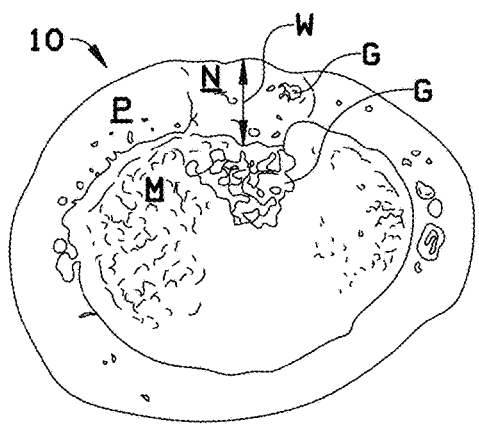
FIG. 6A-6D are histological image for new bone formation and bone healing after 12 weeks.
Figure 6B:
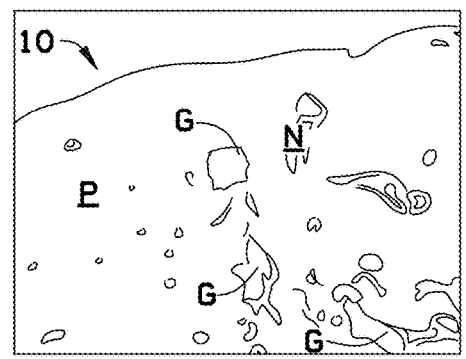
Figure 6C:
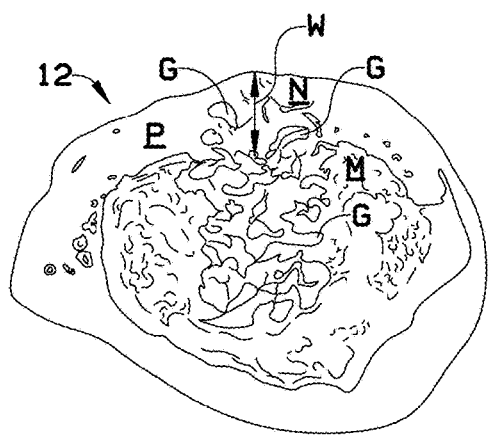
Figure 6D:
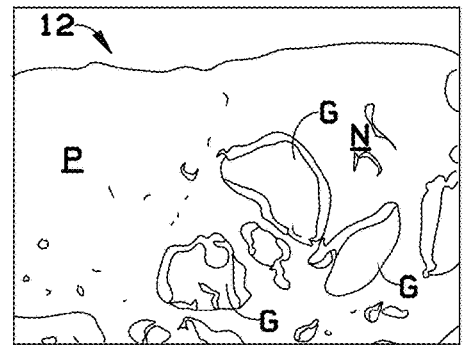

FIG. 5 shows a Fourier Transform Infrared Spectrophotometer (FTIR) analysis which measures how well a sample absorbs light at various wavelengths and by correlating these wavelengths to known standards. Here, the higher line represents embodiments of the present invention and the lower line represents test results for Geistlich Bio-Oss®. While the lines follow similar patterns, indicating similar substances, the present invention absorbs greater light indicating fewer impurities.

The preparation of natural hydroxyapatite granules with the high specific surface area due to inducing polygonal and irregular shape of granules through fracturing and granuling chemically soaked bone blocks not only exceeds products presently on the market in these measures, but also achieves good results in patients. FIGS. 6A through 6D show histological image for new bone formation and bone healing after 12 weeks after insertion of test sample 10 of the present invention and control sample 12 which is prior art. In both cases, bone marrow M is immediately adjacent to preexisting bone P. Bone graft G is inserted to cause new bone to grow.

Figure 7A:
FIG. 7A-7D show photographs of an embodiment of the invention.
Figure 7B:
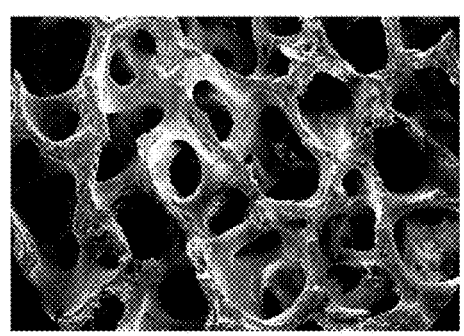
Figure 7C:
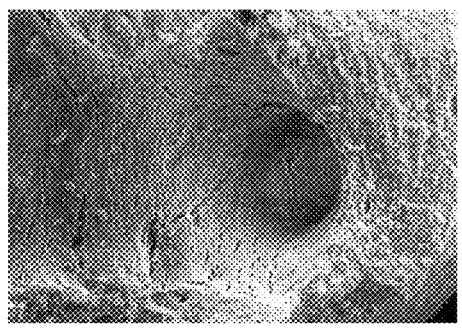
Figure 7D:
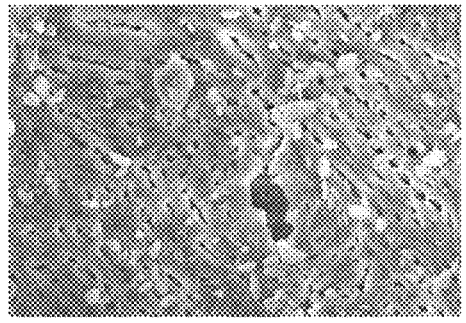

Note that in test sample 10, bone graft G has merged with preexisting bone P to create new bone of a substantial width W. However, control sample 12 has granules still remaining from bone graft G which shows that there is a slower rate in bioresorption compared to test sample 10. These advantages are reinforced in the following photographs. FIG. 7A shows granules of bone graft G. FIG. 7B shows the macropore of granules of bone graft G. FIG. 7C shows the mesopore of granules of bone graft G. FIG. 7D shows the micropore of granules of bone graft G.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A process for extracting natural hydroxyapatite from bone to make granules for a bone graft; the process comprising:
    soaking and boiling raw cancellous bone in deionized water to remove lipids, blood components, and proteins;
    washing the bone in deionized water;
    drying the bone a first time creating a washed cancellous bone;
    segregating the washed cancellous bone with densified porous structure, having a density above 1.6 g/ml from other washed cancellous bone;
    soaking the cancellous bone with densified porous structure in a solution of sodium hydroxide;
    soaking the cancellous bone with densified porous structure in a solution of hydrogen peroxide;
    washing the cancellous bone with densified porous structure in deionized water
    drying the bone a second time;
    sintering the cancellous bone with densified porous structure;
    fracturing the cancellous bone with densified porous structure into the granules for the bone graft.

2. The process of claim 1, wherein drying the bone the first time is done in an oven at a temperature between 60 and 100 degrees centigrade.

3. The process of claim 1, wherein soaking the cancellous bone with densified porous structure in the solution of sodium hydroxide for 1 to 12 hours with between 3 ml and 50 ml of sodium hydroxide used per gram of the cancellous bone with densified porous structure.

4. The process of claim 1, wherein soaking the cancellous bone with densified porous structure in the solution of hydrogen peroxide for 6 to 60 hours with between 3 ml and 50 ml of hydrogen peroxide used per gram of the cancellous bone with densified porous structure.

5. The process of claim 1, wherein sintering the cancellous bone with densified porous structure at 200-600 degrees centigrade for 1-50 hours with a heating rate of 0.01° C./min to 10° C./min.

6. The process of claim 1, wherein the graunles have less than or equal to 400 ppm of crude protein.

7. The process of claim 1, wherein the granules are characterized by an x-ray diffraction pattern comprising peaks expressed in degrees two-theta at about 25 degree, about 30 degree, about 39.5.degree, about 46 degree and about 49 degree.

8. The process of claim 1, wherein the granules have a specific surface area greater than 110 g/m2.

9. A process for extracting natural hydroxyapatite from bone to make granules for a bone graft; the process comprising:
    soaking and boiling raw cancellous bone in deionized water to remove lipids, blood components, and proteins;
    washing the bone in deionized water;
    drying the bone a first time creating a washed cancellous bone;
    segregating the washed cancellous bone with densified porous structure from other washed cancellous bone;
    soaking the cancellous bone with densified porous structure in a solution of sodium hydroxide;
    soaking the cancellous bone with densified porous structure in a solution of hydrogen peroxide;
    washing the cancellous bone with densified porous structure in deionized water
    drying the bone a second time;
    sintering the cancellous bone with densified porous at 200-600 degrees centigrade for 1-50 hours with a heating rate of 0.01° C./min to 10° C./min until the granules are characterized by an x-ray diffraction pattern comprising peaks expressed in degrees two-theta at about 25 degree, about 30 degree, about 39.5.degree, about 46 degree and about 49 degree;
    fracturing the cancellous bone with densified porous structure into the granules for the bone graft.

10. The process of claim 9, wherein drying the bone the first time is done in an oven at a temperature between 60 and 100 degrees centigrade.

11. The process of claim 9, wherein soaking the cancellous bone with densified porous structure in the solution of sodium hydroxide for 1 to 12 hours with between 3 ml and 50 ml of sodium hydroxide used per gram of the cancellous bone with densified porous structure.

12. The process of claim 9, wherein soaking the cancellous bone with densified porous structure in the solution of hydrogen peroxide for 6 to 60 hours with between 3 ml and 50 ml of hydrogen peroxide used per gram of the cancellous bone with densified porous structure.

13. The process of claim 9, wherein the granules have less than or equal to 400 ppm of crude protein.

14. The process of claim 9, wherein the granules have a specific surface area greater than 110 g/m2.

* * * * *